US009782743B2

(12) United States Patent
Iida et al.

(10) Patent No.: US 9,782,743 B2
(45) Date of Patent: Oct. 10, 2017

(54) ADSORBENT FOR ADSORBING VIRUS AND/OR BACTERIUM, CARBON/POLYMER COMPOSITE AND ADSORBENT SHEET

(71) Applicant: Sony Corporation, Tokyo (JP)

(72) Inventors: Hironori Iida, Kanagawa (JP); Shun Yamanoi, Kanagawa (JP); Machiko Minatoya, Tokyo (JP); Seiichiro Tabata, Kanagawa (JP); Shinichiro Yamada, Kanagawa (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 15/137,351

(22) Filed: Apr. 25, 2016

(65) Prior Publication Data

US 2016/0236168 A1 Aug. 18, 2016

Related U.S. Application Data

(63) Continuation of application No. 13/985,184, filed as application No. PCT/JP2012/000726 on Feb. 3, 2012, now abandoned.

(30) Foreign Application Priority Data

Feb. 21, 2011 (JP) .................................. 2011-034571
Dec. 8, 2011 (JP) .................................. 2011-268944

(51) Int. Cl.
  *B01J 20/20* (2006.01)
  *B01J 20/28* (2006.01)
  (Continued)

(52) U.S. Cl.
  CPC .......... *B01J 20/20* (2013.01); *B01J 20/2803* (2013.01); *B01J 20/2808* (2013.01);
  (Continued)

(58) Field of Classification Search
  None
  See application file for complete search history.

(56) References Cited

U.S. PATENT DOCUMENTS

2002/0197547 A1 12/2002 Haggquist
2005/0266749 A1 12/2005 De Ruiter
(Continued)

FOREIGN PATENT DOCUMENTS

CN 101541676 A 9/2009
EP 2060535 A1 5/2009
(Continued)

OTHER PUBLICATIONS

Donald et al., Effects of activation agents and intrinsic minerals on pore development in activated carbons derived from a Canadian peat. Materials Letters 65.4 (2011) 744-747.
(Continued)

*Primary Examiner* — Richard M Rump
(74) *Attorney, Agent, or Firm* — Wolf, Greenfield & Sacks, P.C.

(57) ABSTRACT

[Object]To provide an adsorbent, an adsorbent sheet, and a carbon/polymer composite for adsorbing a virus having further improved virus adsorption capability.
[Solving Means]
An adsorbent for adsorbing a virus according to the present invention has a specific surface area value as measured by the nitrogen BET method of 10 m$^2$/g or more and a pore volume as measured by the BJH method of 0.1 cm$^3$/g or more. An adsorbent sheet for adsorbing a virus according to the present invention includes a porous carbonaceous material having a specific surface area value as measured by the nitrogen BET method of 10 m$^2$/g or more and a pore volume as measured by the BJH method of 0.1 cm$^3$/g or more. A carbon/polymer composite for adsorbing a virus according to the present invention includes a porous carbonaceous
(Continued)

material having a specific surface area value as measured by the nitrogen BET method of 10 m²/g or more and a pore volume as measured by the BJH method of 0.1 cm³/g or more; and a binder.

20 Claims, 6 Drawing Sheets

(51) Int. Cl.
B01J 20/30 (2006.01)
C01B 31/08 (2006.01)
C12N 11/14 (2006.01)
A61L 9/16 (2006.01)

(52) U.S. Cl.
CPC ... B01J 20/28033 (2013.01); B01J 20/28057 (2013.01); B01J 20/28059 (2013.01); B01J 20/28069 (2013.01); B01J 20/28083 (2013.01); B01J 20/28085 (2013.01); B01J 20/28088 (2013.01); B01J 20/30 (2013.01); C01B 31/08 (2013.01); C12N 11/14 (2013.01); A61L 9/16 (2013.01); *A61L 2209/22* (2013.01); *B01J 2220/485* (2013.01); *B01J 2220/4825* (2013.01); *B01J 2220/4875* (2013.01)

(56) References Cited

U.S. PATENT DOCUMENTS

| 2009/0038632 | A1 | 2/2009 | Cashmore et al. |
| 2010/0069507 | A1 | 3/2010 | Tabata et al. |
| 2010/0291167 | A1 | 11/2010 | Iida et al. |
| 2011/0135561 | A1 | 6/2011 | Tabata et al. |
| 2011/0223494 | A1 | 9/2011 | Feaver et al. |
| 2011/0244012 | A1 | 10/2011 | Iida et al. |
| 2012/0231250 | A1 | 9/2012 | Minatoya et al. |
| 2013/0310253 | A1 | 11/2013 | Tabata et al. |
| 2013/0315817 | A1 | 11/2013 | Yamanoi et al. |
| 2013/0324398 | A1 | 12/2013 | Iida et al. |
| 2014/0011666 | A1 | 1/2014 | Yoshizaki et al. |
| 2015/0118477 | A1 | 4/2015 | Iida et al. |

FOREIGN PATENT DOCUMENTS

| EP | 2324854 A1 | 5/2011 |
| EP | 2412432 A1 | 2/2012 |
| JP | 05-049921 | 3/1993 |
| JP | 2005-060849 | 3/2005 |
| JP | 2008-273816 | 11/2008 |
| JP | 2008-273914 | 11/2008 |
| JP | 2009-173523 | 8/2009 |
| JP | 2010-100516 A | 5/2010 |
| JP | 2010-104979 | 5/2010 |
| JP | 2011-225521 | 11/2011 |
| JP | 2012-045538 A | 3/2012 |
| WO | WO 2010-013785 A1 | 2/2010 |
| WO | WO 2010/018855 | 2/2010 |

OTHER PUBLICATIONS

Luisa et al., On comparing BJH and NLDFT pore-size distributions determined from N2 sorption on SBA-15 substrata. Physical Chemistry Chemical Physics 5.9 (2003) 1859-1866.
U.S. Appl. No. 13/053,558, filed Mar. 22, 2011, Iida et al.
U.S. Appl. No. 14/591,666, filed Jan. 7, 2015, Iida et al.
U.S. Appl. No. 12/741,967, filed May 7, 2010, Iida et al.
U.S. Appl. No. 13/411,020, filed Mar. 2, 2012, Minatoya et al.
U.S. Appl. No. 13/983,330, filed Aug. 2, 2013, Tabata et al.
U.S. Appl. No. 13/984,586, filed Aug. 9, 2013, Yamanoi et al.
U.S. Appl. No. 13/985,184, filed Aug. 13, 2013, Iida et al.
U.S. Appl. No. 14/006,187, filed Sep. 19, 2013, Yoshizaki et al.

ADSORBENT FOR ADSORBING VIRUS AND/OR BACTERIUM, CARBON/POLYMER COMPOSITE AND ADSORBENT SHEET

RELATED APPLICATIONS

The present application is a continuation of U.S. Patent Application Serial No. 13/985,184, filed on Aug. 13, 2013, which is a U.S. national stage filing under 35 U.S.C. §371 of International Application No. PCT/JP2012/000726, filed on Feb. 3, 2012, which claims priority to Japanese Patent Application No. JP 2011-034571, filed on Feb. 21, 2011, and Japanese Patent Application No. JP 2011-268944, filed on Dec. 8, 2011, all of which are hereby incorporated by reference in their entireties.

TECHNICAL FIELD

The present invention relates to an adsorbent for adsorbing a virus and/or a bacterium and an adsorbent sheet.

BACKGROUND ART

Activated carbon made from traditional coconut husks and petroleum pitches is used as a material for a number of filters, and draws an attention as an adsorbent for adsorbing a virus (see, for example, Japanese Patent Application Laid-open No. 2008-273914).

Patent Document 1: Japanese Patent Application Laid-open No. 2008-273914

SUMMARY OF INVENTION

Problem to be Solved by the Invention

Since the virus adsorbent using the traditional activated carbon includes activated carbon mainly having micro pores with a size of 2 nm or less, virus adsorption capability and bacterial adsorption capability are insufficient. Through studies by the present inventors, it has been revealed that the adsorption capability should be further improved.

Accordingly, an object of the present disclosure is to provide an adsorbent, a carbon/polymer composite using the adsorbent, and an adsorbent sheet for adsorbing a virus and/or a bacterium (in other words, adsorbing a virus, or adsorbing a bacterium, or adsorbing a virus and a bacterium) having further improved virus adsorption capability and/or bacterial adsorption capability.

Means for Solving the Problem

An adsorbent for adsorbing a virus and/or a bacterium according to a first aspect of the present disclosure in order to achieve the above-described object comprises a porous carbonaceous material having a specific surface area value as measured by the nitrogen BET method of 10 m²/g or more and a pore volume as measured by the BJH method of 0.1 cm³/g or more.

An adsorbent for adsorbing a virus and/or a bacterium according to a second aspect of the present disclosure in order to achieve the above-described object comprises a porous carbonaceous material having a specific surface area value as measured by the nitrogen BET method of 10 m²/g or more, and a total pore volume determined by the Non Localized Density Functional Theory of 0.1 cm³/g or more, of which the pores have diameters in the range from $1\times10^{-9}$ m to $5\times10^{-7}$ m.

An adsorbent for adsorbing a virus and/or a bacterium according to a third aspect of the present disclosure in order to achieve the above-described object comprises a porous carbonaceous material having a specific surface area value as measured by the nitrogen BET method of 10 m²/g or more, at least one peak in a pore diameter distribution determined by the Non Localized Density Functional Theory in the range from 3 nm to 20 nm, and a ratio of the total volume of the pores with diameters in the range from 3 nm to 20 nm, being 0.2 or more of the total pore volume.

A carbon/polymer composite for adsorbing a virus and/or a bacterium according to the first aspect of the present disclosure in order to achieve the above-described object comprises the porous carbonaceous material according to the first aspect of the present invention and a binder.

A carbon/polymer composite for adsorbing a virus and/or a bacterium according to the second aspect of the present disclosure in order to achieve the above-described object comprises the porous carbonaceous material according to the second aspect of the present invention and a binder.

A carbon/polymer composite for adsorbing a virus and/or a bacterium according to the third aspect of the present disclosure in order to achieve the above-described object comprises the porous carbonaceous material according to the third aspect of the present invention and a binder.

An adsorbent sheet for adsorbing a virus and/or a bacterium for adsorbing a virus and/or a bacterium according to the first aspect of the present disclosure in order to achieve the above-described object comprises the porous carbonaceous material according to the first aspect of the present invention and a support member.

An adsorbent sheet for adsorbing a virus and/or a bacterium for adsorbing a virus and/or a bacterium according to the second aspect of the present disclosure in order to achieve the above-described object comprises the porous carbonaceous material according to the second aspect of the present invention and a support member.

An adsorbent sheet for adsorbing a virus and/or a bacterium for adsorbing a virus and/or a bacterium according to the third aspect of the present disclosure in order to achieve the above-described object comprises the porous carbonaceous material according to the third aspect of the present invention and a support member.

Effect of the Invention

In the adsorbent, the adsorbent, the carbon/polymer composite, and the adsorbent sheet for adsorbing a virus and/or a bacterium according to the first to third aspects of the present disclosure, the specific surface area value of the porous carbon material used, the value of the pore volume, and the pore diameter distribution are defined, thereby adsorbing a virus and/or a bacterium with high efficiency.

MODES FOR CARRYING OUT THE INVENTION

Figure 1:
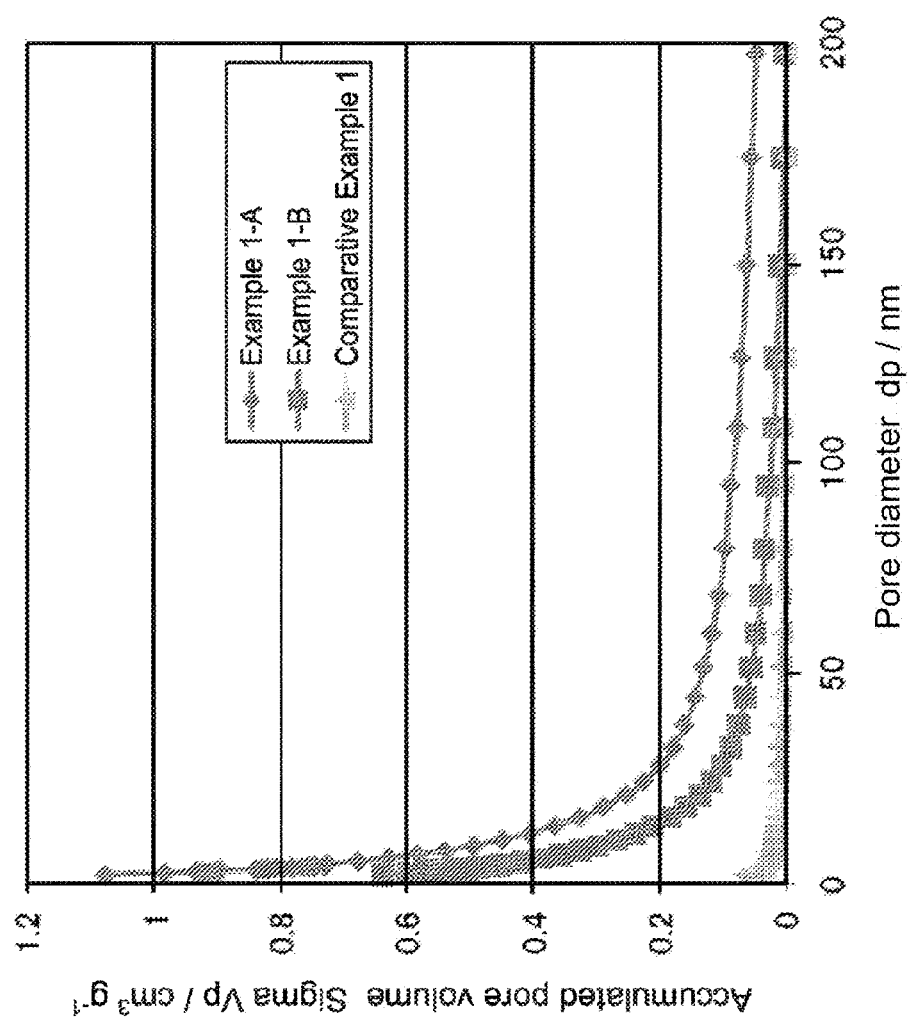
FIG. 1 A graph showing accumulated measurement results of the pore volumes about the adsorbents according to Example 1-A, Example 1-B and Comparative Example 1.

Hereinafter, embodiments of the present disclosure will be described with reference to the drawings. The present disclosure is not limited to the embodiments, and various numerical values and materials mentioned in the description of the embodiments are merely examples. The embodiments will be described in the following order.

1. An adsorbent, a carbon/polymer composite, an adsorbent sheet for adsorbing a virus and/or a bacterium according to the first to third aspects of the present disclosure, general description
2. Example 1 (the adsorbent, the carbon/polymer composite, the adsorbent sheet for adsorbing a virus and/or a bacterium according to the first to third aspects of the present disclosure)
3. Example 2 (other application example of Example 1)
4. Example 3 (still other application example of Example 1)
5. Example 4 (still other application example of Example 1), others In the following description, the adsorbent for adsorbing a virus and/or a bacterium according to the first to third aspects of the present disclosure may be simply called "the adsorbent of the present disclosure". The carbon/polymer composite according to the first to third aspects of the present disclosure may be simply called "the carbon/polymer composite of the present disclosure". The adsorbent sheet according to the first to third aspects of the present disclosure may be simply called "the adsorbent sheet of the present disclosure". The adsorbent of the present disclosure, the carbon/polymer composite of the present disclosure, and the adsorbent sheet of the present disclosure may be simply called "the present disclosure". The porous carbon material constituting the adsorbent of the present disclosure, the carbon/polymer composite of the present disclosure, and the adsorbent sheet of the present disclosure may be called "the porous carbon material in the present disclosure".

[An Adsorbent, a Carbon/Polymer Composite, an Adsorbent Sheet for Adsorbing a Virus and/or a Bacterium According to the First to Third Aspects of the Present Disclosure, General Description]

In the present disclosure, the porous carbon material is made from the plant-based material. Non-limiting examples of the plant-based material are chaff and straws of rice (paddy), barley, wheat, rye, Japanese millet and foxtail millet; coffee beans, tea leaves (for example, leaves of green tea, black tea and the like); sugar canes (in particular, bagasse); corns (in particular, core of corn); fruit peels (for example, citrus peels such as mandarin orange peel, banana peel and the like); reeds; Wakame seaweed stems (*Undaria pinnatifida*); terrestrial vascular plants; ferns; bryophytes; algae; and marine algae. These materials may be used alone, and plural types of such materials may alternatively be used in combination. The shape and the form of the plant-based material are not especially limited. For example, the plant-based material may be chaff or straw itself, or the dried product. In addition, in terms of food processing of beer, liqueur or the like, a residue of various processing including fermentation, roasting, or extracting, can be applied. In particular, from the standpoint of recycling the industrial wastes, it is desirable that chaff and straws after processing, e.g., after threshing, are used. These chaff and straws after processing are easily available in large amounts from, for example, agricultural cooperatives, alcoholic beverage makers, food companies and food processing companies.

In the adsorbent sheet of the present disclosure including the above-described preferred embodiments, a woven fabric and a non-woven fabric can be used as the support member. Cellulose, polypropylene and polyester can be used as the material of the support member. Further, the adsorbent sheet can have the embodiments that the porous carbon material in the present disclosure is sandwiched between the support members, and that the porous carbon material is kneaded with the support member. As the binder included in the carbon/polymer composite of the present disclosure, carboxyl nitrocellulose can be used, for example.

The present disclosure can be used for purifying water or air, generally fluid. The adsorbent of the present disclosure can be used as a sheet form, can be used by filling it into a column or a cartridge, can be used by shaping into a desired shape using a binder (a binding agent), or can be used as powder. When a purifier or the adsorbent is used by dispersing it in a solution, the surface can be hydrophobically or hydrophilically treated and can be then used. The adsorbent sheet of the present disclosure or the carbon/polymer composite of the present disclosure can be made into a filter for an air purifier, a mask, a pair of protective gloves, or protective shoes.

When the porous carbon material in the present disclosure is made from a plant-based material containing silicon (Si), it is not especially limited, but the porous carbon material is made from the plant-based material containing 5% by mass or more of silicon (Si), containing 5% by mass or less of silicon (Si), desirably 3% by mass or of less silicon (Si), and more desirably 1% by mass or less of silicon (Si).

The porous carbon material in the present disclosure can be produced, for example, by carbonizing the plant-based material at 400° C. to 1400° C., and then treating the material with acid or alkali. In the method of producing the porous carbon material according to the present disclosure (hereinafter simply referred to as "the method of producing the porous carbon material"), the material obtained by carbonizing the plant-based material at 400° C. to 1400° C., which is not yet treated with acid or alkali is referred to as "the porous carbon material precursor" or "the carbonaceous substance".

In the method of producing the porous carbon material, after the acid or alkali treatment, activation treatment can be performed. Or, after the activation treatment, the acid or alkali treatment may be performed. In the method of producing the porous carbon material including the above-described desirable form, although it depends on the plant-based material being used, the plant-based material may be heated (pre-carbonized) at a temperature lower than the carbonizing temperature (for example, at 400° C. to 700° C.) in an oxygen-free state before the plant-based material is carbonized. As a result of extracting a tar component that would be produced during the carbonization, the tar component that would be produced during the carbonization can be reduced or removed. The oxygen-free state can be achieved by, for example, providing an inert gas atmosphere including a nitrogen gas or an argon gas, providing a vacuum atmosphere, or almost steaming and baking the plant-based material. In the method of producing the porous carbon material, although it depends on the plant-based material being used, the plant-based material may be immersed into alcohols (for example, methyl alcohol, ethyl alcohol and isopropyl alcohol) in order to decrease mineral components and a water content or to prevent odor generation during the carbonization. Also, in the method of producing the porous carbon material, pre-carbonization may be performed thereafter. The plant-based material that produces a large amount of pyroligneous acid (tar and light crude oil) is an example that is desirably heated under the inert gas atmosphere. Seaweeds, which is the plant-based material containing a large amount of iodine and various minerals, is an example that is desirably pretreated with alcohol.

In the method of producing the porous carbon material, the plant-based material is carbonized at 400° C. to 1400° C. The "carbonization" herein means that organic substances (the plant-based material in the porous carbon material according to the present disclosure) are typically heated to convert them into carbonaceous substance (for example, see JIS M0104-1984). An example of the atmosphere for carbonization is an oxygen-free atmosphere. Specifically, there are a vacuum atmosphere, an inert gas atmosphere including a nitrogen gas or an argon gas, and an atmosphere where the plant-based material is almost steamed and baked. The rate of temperature increase to the carbonization temperature is not limited, but can be 1° C./min or more, desirably 3° C./min or more, more desirably 5° C./min or more under such atmosphere. The upper limit of the carbonization time may be 10 hours, desirably 7 hours and more desirably 5 hours, but not limited thereto. The lower limit of the carbonization time may be such that the plant-based material is surely carbonized. The plant-based material may be pulverized to the desired particle size, or classified, as necessary. The plant-based material may be pre-cleaned. Also, the resultant porous carbon material precursor or the porous carbon materials may be pulverized to the desired particle size, or classified, as necessary. In addition, the processed porous carbon material by the activation treatment may be pulverized to the desired particle size, or classified, as necessary. Furthermore, the finally resultant porous carbon material may be sterilized. The furnace used for carbonization is not limited in terms of a shape, a configuration and a structure, and may be a continuous furnace or a batch furnace.

In the method of producing the porous carbon material, as described above, the activation treatment can increase the numbers of micro pores each having a pore diameter of not greater than 2 nm (which will be described later). Examples of the activation treatment are gas activation and chemical activation. In the gas activation, oxygen, water vapor, carbon dioxide gas, air or the like can be used as an activator. Under the gas atmosphere, the porous carbon material is heated at 700° C. to 1400° C., desirably 700° C. to 1000° C., more desirably 800° C. to 1000° C. for several tens of minutes to several hours, so that the microstructure is grown by the volatile components and carbon molecules in the porous carbon material. More specifically, the heating temperature may be selected based on the types of the plant-based material, the kinds and concentration of the gas and the like, as necessary. In the chemical activation, the porous carbon material is activated by using zinc chloride, iron chloride, calcium phosphate, calcium hydroxide, magnesium carbonate, potassium carbonate, sulfate or the like is used for activation instead of oxygen and water vapor used in the gas activation, and is cleaned with hydrochloric acid. The pH of the porous carbon material is adjusted by using an alkaline solution. Then, the porous carbon material is dried.

The surface of the porous carbon material in the present disclosure may be chemical treated or molecular modified. For example, as one of the chemical treatments, a nitric acid treatment is performed to produce carboxyl groups on the surface. By the similar treatment as the activation treatment with water vapor, oxygen, alkali or the like, various functional groups such as a hydroxyl group, a carboxyl group, a ketone group or an ester group can be produced on the surface of the porous carbon material. In addition, when the porous carbon material is chemically reacted with chemical species or protein containing a hydroxyl group, a carboxyl group, an amino group or the like, the molecular modification may be possible.

In the method of producing the porous carbon material, silicon components are removed by the acid or alkali treatment from the carbonized plant-based material. The silicon components may be silicon oxides such as silicon dioxide, silicon oxide and a salt of silicon oxide. By removing the silicon components in the carbonized plant-based material, there can be provided the porous carbon material having high specific surface area. In some cases, the silicon components in the carbonized plant-based material may be removed by a dry etching method.

The porous carbon material in the present disclosure may contain magnesium (Mg), potassium (K), calcium (Ca), non-metal elements such as phosphorous (P) and sulfur (S), and metal elements such as transition elements. The amount of magnesium (Mg) may be from 0.01% by mass to 3% by mass, the amount of potassium (K) may be from 0.01% by mass to 3% by mass, the amount of calcium (Ca) may be from 0.05% by mass to 3% by mass, the amount of phosphorous (P) may be from 0.01% by mass to 3% by mass, and the amount of sulfur (S) may be from 0.01% by mass to 3% by mass, as examples. In terms of an increase in the specific surface area value, the amounts of these elements are desirably small. It should be appreciated that the porous carbon material may contain elements other than those described above, and the amounts of various elements as described above may be changed.

In the porous carbon material in the present disclosure, various elements can be analyzed by energy dispersive spectrometry (EDS) using an energy dispersive X-ray spectrometer (for example, JED-2200F manufactured by JEOL Ltd.). The measurement conditions may include, for example, a scanning voltage of 15 kV and an illumination current of 10 μA.

The porous carbon material in the present disclosure has many pores. The pores include "mesopores" having a pore diameter in the range from 2 nm to 50 nm, "micropores" having a pore diameter less than 2 nm and "macropores" having a pore diameter exceeding 50 nm. Specifically, the mesopores have many pores having a size of 20 nm or less, especially 10 nm or less, for example. The porous carbon material according to the present disclosure desirably has a pore volume by the BJH method of 0.1 cm$^3$/g or more, desirably 0.2 cm$^3$/g or more, more desirably 0.3 cm$^3$/g or more, and even more desirably 0.5 cm$^3$/g or more.

It is desirable that the porous carbon material in the present disclosure desirably has the specific surface area value by the nitrogen BET method (hereinafter may be simply referred to as "the specific surface area value") of 50 m²/g or more, more desirably 100 m²/g or more, most and even more desirably 400 m²/g or more in order to provide higher functionality.

The nitrogen BET method is to measure the adsorption isotherm by adsorbing and desorbing admolecules, i.e. nitrogen, to/from an adsorbent (herein, the porous carbon material), and analyze the measured data by the BET equation represented by the equation (1). Based on the method, the specific surface area, the pore volume and the like can be calculated. Specifically, when the specific surface area value is calculated on the basis of the nitrogen BET method, the adsorption isotherm is first measured by adsorbing and desorbing the admolecules, i.e., nitrogen, to/from the porous carbon material. Then, $[p/\{V_a(p_0-p)\}]$ is calculated from the measured adsorption isotherm based on the equation (1) or the deformed equation (1') and is plotted to the relative pressure in equilibrium $(p/p_0)$. The plot is considered as a straight line, and the slope s $(=[(C-1)/(C \cdot V_m)])$ and the intercept i $(=[1/(C \cdot V_m)])$ are calculated based on least squares method. The $V_m$ and $C$ are calculated from the calculated slope s and the intercept i based on the equations (2-1) and (2-2). The specific surface area $a_{sBET}$ is calculated from $V_m$ based on the equation (3) (see BELSORP-mini and BELSORP analysis software manual, pp. 62-66, made by BELL Japan Inc.). The nitrogen BET method is the measuring method in accordance with JIS R 1626-1996 "Measuring methods for the specific surface area of fine ceramic powders by gas adsorption using the BET method".

$$V_a = (V_m \cdot C \cdot p)/[(p-p_0)\{1+(C-1)(p/p_0)\}] \quad (1)$$

$$[p/\{V_a(p_0-p)\}] = [(C-1)/(C \cdot V_m)](p/p_0) + [1/(C \cdot V_m)] \quad (1')$$

$$V_m = 1/(s+i) \quad (2\text{-}1)$$

$$C = (s/i)+1 \quad (2\text{-}2)$$

$$a_{sBET} = (V_m \cdot L \cdot \sigma)/22414 \quad (3)$$

where,
$V_a$: Adsorbed amount
$V_m$: Adsorbed amount of monolayer
p: Nitrogen pressure in equilibrium
$p_0$: Saturated vapor pressure of nitrogen
L: The Avogadro number
σ: Adsorbed section area of nitrogen When the pore volume $V_p$ is calculated by the nitrogen BET method, the adsorption data of the measured adsorption isotherm is, for example, linearly interpolated to determine the adsorbed amount V at relative pressure set for calculating the pore volume. The pore volume $V_p$ can be calculated from the adsorbed amount V based on the equation (4) (see BELSORP-mini and BELSORP analysis software manual, pp. 62-66, made by BELL Japan Inc.). The pore volume determined by the nitrogen BET method may be referred to simply as "the pore volume".

$$V_p = (V/22414) \times (M_g/\rho_g) \quad (4)$$

where,
V: Adsorbed amount at relative pressure
$M_g$: Molecular weight of nitrogen
$\rho_g$: Density of nitrogen The pore diameter of the mesopores can be calculated as, for example, the pore distribution from the change rate of the pore volume to the pore diameter based on the BJH method. The BJH method is widely used as a method for pore diameter distribution analysis. When the pore diameter distribution is analyzed by the BJH method, the adsorption isotherm is first measured by adsorbing and desorbing the admolecules, i.e., nitrogen, to/from the porous carbon material. Then, based on the measured adsorption isotherm, the thickness of the adsorbed layer is determined when the adsorbed molecules (for example, nitrogen) that fill the pores are gradually adsorbed/desorbed, and the inner diameter (twice a core diameter) of the pores is determined. Based on the equation (5), the pore radius $r_p$ is calculated. Based on the equation (6), the pore volume is calculated. Then, the pore distribution curve is obtained by plotting the change rate of the pore volume $(dV_p/dr_p)$ to the pore diameter $(2r_p)$ based on the pore radius and the pore volume (see BELSORP-mini and BELSORP analysis software manual, pp. 85-88, made by BELL Japan Inc.).

$$r_p = t + r_k \quad (5)$$

$$V_{pn} = R_n \cdot dV_n - R_n \cdot dt_n \cdot c \cdot \Sigma A_{pj} \quad (6)$$

where, $$R_n = r_{pn}^2/(r_{kn-1} + dt_n)^2 \quad (7)$$

where,
$r_p$: Pore radius
$r_k$: Core radius (inner diameter/2) when the adsorbed layer having a thickness of t is adsorbed on the inner wall of the pore having the pore radius $r_p$ at the pressure
$V_{pn}$: Pore volume at the time of n-th adsorption/desorption of nitrogen
$dV_n$: Amount of change at the time of n-th adsorption/desorption of nitrogen
$dt_n$: Amount of change in the thickness $t_n$ at the time of n-th adsorption/desorption of nitrogen
$r_{kn}$: Core radius at the time of n-th adsorption/desorption of nitrogen
c: Fixed value
$r_{pn}$: Pore radius at the time of n-th adsorption/desorption of nitrogen In addition, $\Sigma A_{pj}$ represents the integration value of the areas of the pore walls from j=1 to j=n-1.

The pore diameter of the micropores can be calculated as, for example, the pore distribution from the change rate of the pore volume to the pore diameter based on the MP method. When the pore distribution is analyzed by the MP method, the adsorption isotherm is first measured by adsorbing nitrogen to the porous carbon material. Then, the adsorption isotherm is converted (t plotted) into the pore volume to the thickness t of the adsorbed layer. The pore distribution curve is obtained based on curvature (amount of change in the pore volume to amount of change in the thickness t of the adsorbed layer) of the plot (see BELSORP-mini and BELSORP analysis software manual, pp. 72-73, 82, made by BELL Japan Inc.).

The Non Localized Density Functional Theory (NLDFT) method specified in JIS Z8831-2:2010 "Pore Size Distribution and Porosity of Powders (Solid Materials)—Part 2: Method of Measuring Mesopores and Macropores using Gas Absorption" and JIS Z8831-3:2010 "Pore Size Distribution and Porosity of Powders (Solid Materials)—Part 3: Method of Measuring Micropores using Gas Absorption" employs a program accompanying the automatic specific surface area/pore distribution measuring apparatus "BELSORP-MAX" manufactured by BELL JAPAN, INC. as an analyzing program. An analysis is carried out using a model having a cylindrical shape and assuming carbon black (CB), as prerequisites for the analysis. Then, a distribution function for pore distribution parameters is set as "no-assumption", and smoothing will be performed ten times on distribution data thus obtained.

The porous carbon material precursor is treated with an acid or alkali. For example, the porous carbon material precursor may be immersed into a water solution of an acid or alkali. Or, the porous carbon material precursor may be reacted with an acid or alkali in the vapor phase. More specifically, the acid treatment may be carried out using an acidic fluorine compound as an acid such as a hydrogen fluoride, hydrofluoric acid, ammonium fluoride, calcium fluoride, or sodium fluoride. When a fluorine compound is used, the amount of fluorine is desirably four times the amount of element silicon in silicon components included in the porous carbon material precursor, and a water solution of the fluorine compound desirably has a concentration of 10 wt % or more. When silicon components (e.g., silicon dioxide) included in the porous carbon material precursor are removed by the use of a hydrofluoric acid, silicon dioxide reacts with the hydrofluoric acid as indicated by chemical formula (A) or (B), and silicon can be eliminated as hydrogen hexafluorosilicate ($H_2SiF_6$) or silicon tetrafluoride ($SiF_4$). Thus, a porous carbon material is obtained. The material may thereafter be washed and dried.

$$SiO_2 + 6HF \rightarrow H_2SiF_6 + 2H_2O \quad (A)$$

$$SiO_2 + 4HF \rightarrow SiF_4 + 2H_2O \quad (B)$$

When the precursor is treated with alkali (base), the alkali may be sodium hydroxide. When a water solution of alkali is used, the pH of the water solution may be 11 or more. When silicon components (e.g., silicon dioxide) included in the porous carbon material precursor are removed by the use of a water solution of sodium hydroxide, silicon dioxide is made to react as indicated by chemical formula (C) by the heating of the water solution of sodium hydroxide. The silicon can be eliminated as sodium silicate ($Na_2SiO_3$). Thus, a porous carbon material is obtained. When the precursor is treated by the reaction caused by sodium hydroxide in the vapor phase, sodium hydroxide in a solid state is heated to cause it to react as indicated by the chemical formula (C). The silicon can be eliminated as sodium silicate ($Na_2SiO_3$). Thus, a porous carbon material is obtained. The material may thereafter be washed and dried.

$$SiO_2 + 2NaOH \rightarrow Na_2SiO_3 + H_2O \quad (C)$$

The porous carbon material according to the present disclosure may be a porous carbon material including holes having three-dimensional regularity, for example, as disclosed in Japanese Unexamined Patent Application Publication No. 2010-106007 (a porous carbon material having what is called an inverse opal structure). Specifically, the porous carbon material has spherical holes in a three dimensional arrangement having an average diameter in the range from $1 \times 10^{-9}$ m to $1 \times 10^{-5}$ m and having a surface area of $3 \times 10^2$ m$^2$/g or more. Desirably, the holes are arranged in a disposition similar to a crystalline structure in a macroscopic point of view. Alternatively, the porous carbon material has holes arranged on a surface thereof in a disposition similar to the alignment of a (111) plane of a face-centered cubic structure in a macroscopic point of view.

EXAMPLE 1

Example 1 relates to the adsorbent for adsorbing a virus and/or a bacterium according to the first to third aspects of the present disclosure, the carbon/polymer composite according to the first to third aspects of the present disclosure, and the adsorbent sheet according to the first to third aspects of the present disclosure.

The adsorbent for adsorbing a virus and/or a bacterium of Example 1 (hereinafter referred simply to as "the adsorbent") includes a porous carbonaceous material having a specific surface area value as measured by the nitrogen BET method of 10 m$^2$/g or more and a pore (mesopore) volume as measured by the BJH method of 0.1 cm$^3$/g or more in accordance with the adsorbent for adsorbing a virus and/or a bacterium according to the first aspect of the present disclosure.

The adsorbent of Example 1 includes a porous carbonaceous material having a specific surface area value as measured by the nitrogen BET method of 10 m$^2$/g or more, and a total pore volume determined by the Non Localized Density Functional Theory of 0.1 cm$^3$/g or more, of which the pores have diameters in the range from $1 \times 10^{-9}$ m to $5 \times 10^{-7}$ m in accordance with the adsorbent for adsorbing a virus and/or a bacterium according to the second aspect of the present disclosure.

Further, the adsorbent of Example 1 includes a porous carbonaceous material having a specific surface area value as measured by the nitrogen BET method of 10 m$^2$/g or more, at least one peak in a pore diameter distribution determined by the Non Localized Density Functional Theory in the range from 3 nm to 20 nm, and a ratio of the total volume of the pores with diameters in the range from 3 nm to 20 nm, being 0.2 or more of the total pore volume in accordance with the adsorbent for adsorbing a virus and/or a bacterium according to the third aspect of the present disclosure.

In Example 1, the porous carbonaceous material is made from chaff of rice (paddy) used as the plant-based material. The porous carbonaceous material of Example 1 is obtained by carbonizing the chaff as the plant-based material, converting it into a carbonaceous substance (a porous carbon material precursor), and then performing an acid treatment. Hereinafter, a method of producing the adsorbent of Example 1 will be explained.

The porous carbon material of Example 1 was obtained by carbonizing the plant-based material at 400° C. to 1400° C., and then treating the material with acid or alkali. In other words, the chaff is heated (pre-carbonized) in an inert gas. Specifically, the chaff is carbonized by heating at 500° C. for 3 hours in a flow of nitrogen gas, and a carbide is obtained. Such a process makes it possible to reduce or eliminate tar components that would be produced at a subsequent carbonizing step. Thereafter, 10 grams of the carbide was put in a crucible made of alumina, and the temperature of the carbide was raised to 800° C. at a rate of 5° C./min in a flow of nitrogen gas (5 liters/min). The carbide was carbonized at 800° C. for one hour and converted into a carbonaceous substance (a porous carbon material precursor), and the substance was cooled down to room temperature. The nitrogen gas was kept flowing during the carbonization and cooling. Next, the porous carbon material precursor was acid-treated by immersion in a water solution of hydrofluoric acid of 46 vol % overnight, and the precursor was washed with water and ethyl alcohol until it reached a pH of 7. Next, the precursor was dried at 120° C. and the temperature of the precursor was raised to 900° C. in a flow of nitrogen gas. Then, the precursor was activated by heating at 900° C. for 3 hours in a flow of water vapor. Thus, the adsorbent of Example 1 could be obtained. Thus-obtained adsorbent is called as an adsorbent of Example 1-A.

By changing firing conditions such as a firing temperature, an adsorbent of Example 1-B was obtained.

As Comparative Example 1, a commercially available adsorbent including coconut husks activated carbon (manufactured by Wako Pure Chemical Industries, Ltd.) was used. As Comparative Example 2, a commercially available polypropylene non-woven mask was used. As Comparative Example 3, a commercially available polypropylene non-woven mask was used. As Comparative Example 4, a commercially available polyester non-woven mask was used.

A nitrogen absorption/desorption test was carried out to find the specific surface areas and the pore volumes, using a measuring apparatus BELSORP-mini (manufactured by BELL JAPAN, INC.). The measurement was carried out at a measurement relative pressure in equilibrium ($p/p_0$) of 0.01 to 0.99. Pore diameter distributions of mesopores and micropores were calculated by conducting a nitrogen absorption/desorption test using the above-mentioned measuring apparatus using the BELSORP analysis program based on the BJH method and the MP method. The pore of the porous carbon material was measured by mercury intrusion method. Specifically, a mercury porosimeter (PAS-CAL440 manufactured by Thermo Fisher Scientific Inc.) was used to conduct the mercury intrusion method. Further, the measurement based on the Non Localized Density Functional Theory (NLDFT) was carried out using a software attached to an automatic specific surface area/pore distribution measuring apparatus "BELSORP-MAX" manufactured by BELL JAPAN, INC. Prior to the measurement, the samples were subjected to drying at 200° C. for 3 hours as a pre-process.

Figure 2:
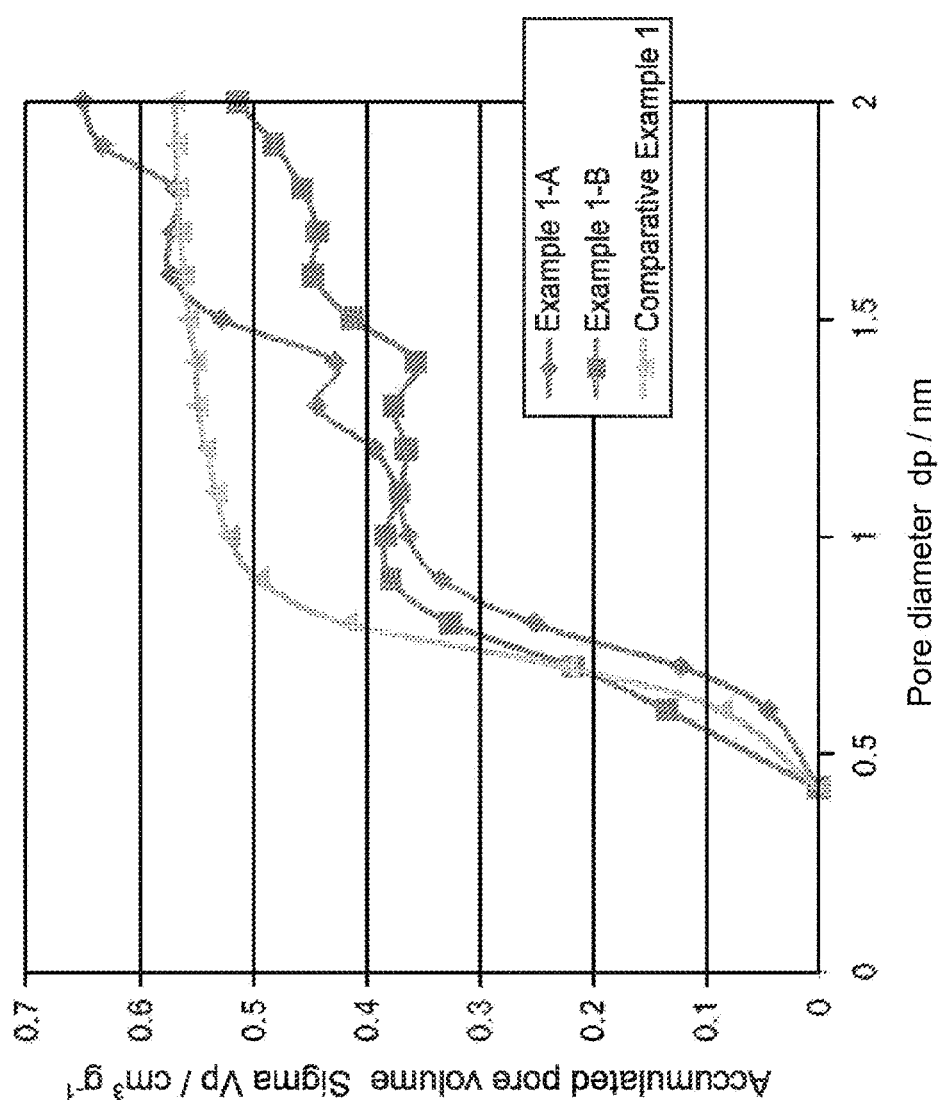
FIG. 2 A graph showing accumulated measurement results of the pore volumes about the adsorbents according to Example 1-A, Example 1-B and Comparative Example 1.
Figure 3:
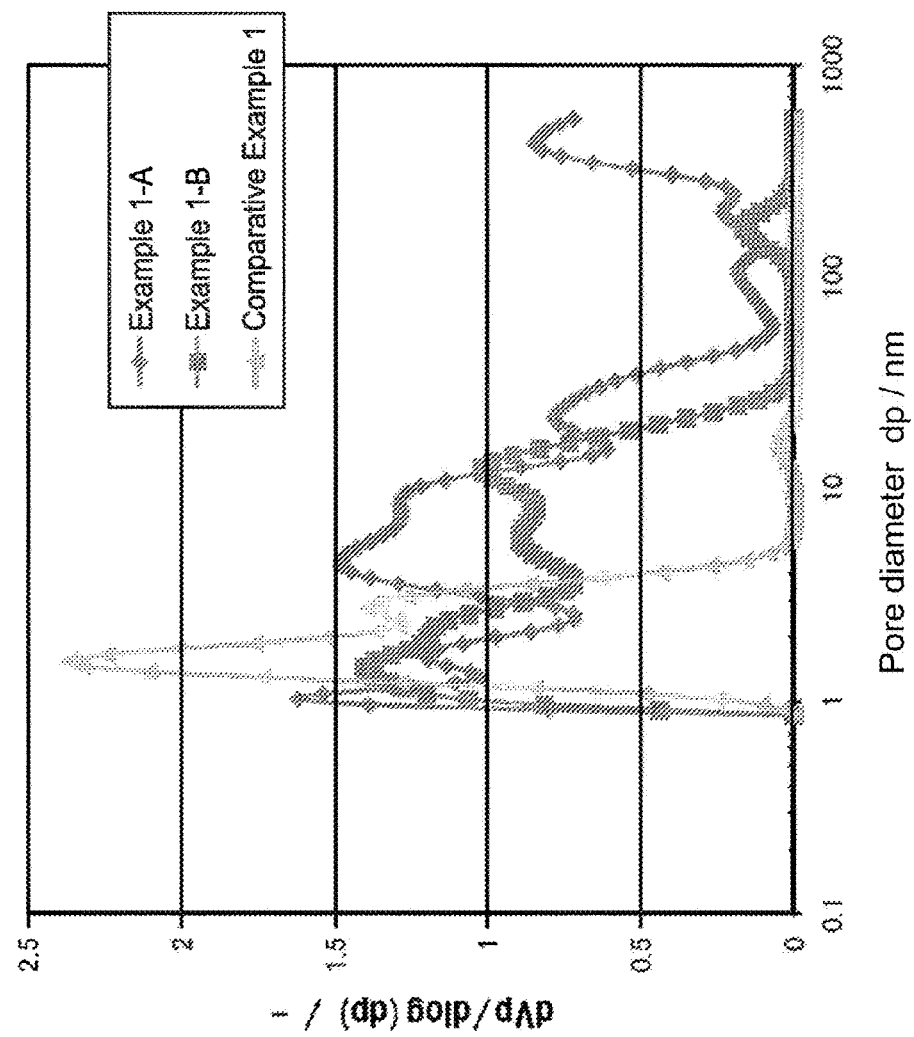
FIG. 3 A graph showing measurement results of pore diameter distributions according to Example 1-A, Example 1-B and Comparative Example 1 determined by Non Localized Density Functional Theory.

The specific surface area and the pore volume of each of the adsorbents of Example 1-A, Example 1-B and Comparative Example 1 and each of the masks of Comparative Example 2 to Comparative Example 4 were measured. Table 1 shows the results. In Table 1, the "specific surface area" and the "total pore volume" refer to a specific surface area and a total pore volume obtained according to the nitrogen BET method. The units are in $m^2/g$ and $cm^3/g$. The "MP method", "BJH method" and "mercury intrusion method" refer to a pore (micropore) volume result measured by the MP method, a pore (mesopore to macropore) volume result measured by the BJH method, and a pore volume result measured by the mercury intrusion method, respectively. The units are in $cm^3/g$. FIGS. 1 and 2 show the results of the measurement of the total pore volume in each of Example 1-A, Example 1-B and Comparative Example 1. Furthermore, FIG. 3 shows the results of the measurement of the pore diameter distribution determined by the Non Localized Density Functional Theory. A ratio of the total volume of the pores each having a pore diameter in the range from 3 nm to 20 nm to the total pore volume is as follows:

Example 1-A: 0.407 (total pore volume: 2.16 $cm^3/g$)

Example 1-B: 0.479 (total pore volume: 1.33 $cm^3/g$)

Comparative Example 1: 0.134 (total pore volume: 0.756 $cm^3/g$)

TABLE 1

| | Specific surface area | Total pore volume | MP method | BJH method | Mercury intrusion method |
|---|---|---|---|---|---|
| Example 1-A | 1700 | 1.54 | 0.651 | 1.08 | 4.12 |
| Example 1-B | 1360 | 1.08 | 0.515 | 0.641 | — |
| Comparative Example 1 | 1270 | 0.57 | 0.570 | 0.070 | 1.50 |
| Comparative Example 2 | <10 | <0.01 | <0.01 | <0.01 | — |
| Comparative Example 3 | <10 | <0.01 | <0.01 | <0.01 | — |
| Comparative Example 4 | 12 | <0.01 | <0.01 | <0.01 | — |

It shows that the adsorbents of Example 1-A and example 1-B have Greater Values in Mesopores to Macropores volume and in pore volume obtained by the mercury intrusion method as compared with the adsorbent of Comparative Example 1.

An antivirus property against influenza A is evaluated for each of the adsorbents of Example 1-A, Example 1-B and Comparative Example 1 and Each of the Masks of Comparative Example 2 to Comparative Example 4. A size of the influenza A is from 80 nm to 120 nm.

Figure 4:
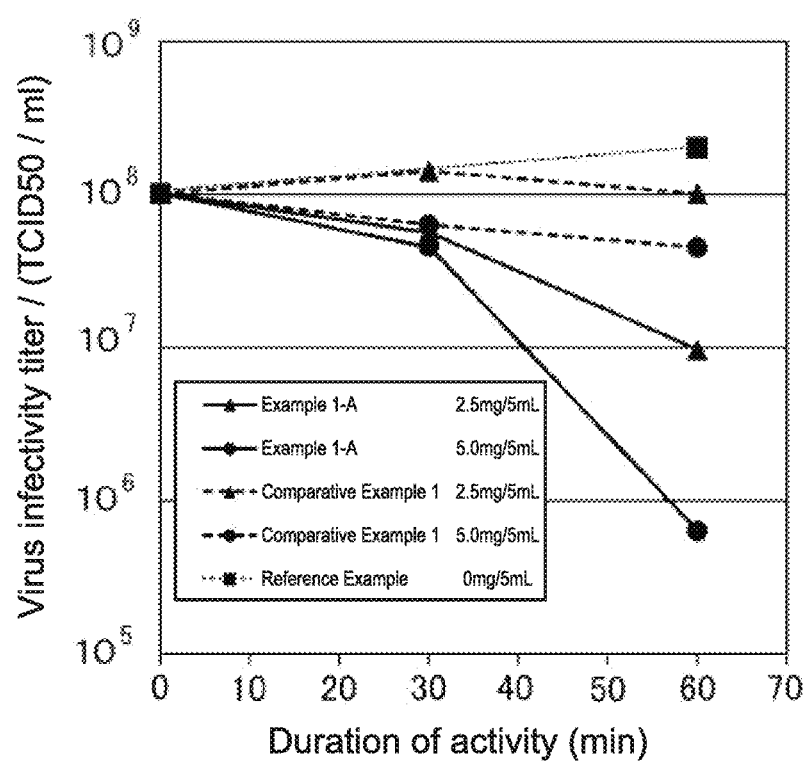
FIG. 4 A graph showing a change in virus infectivity titers to duration of activity of the adsorbents according to Example 1-A, Example 1-B and Comparative Example 1.
Figure 5:
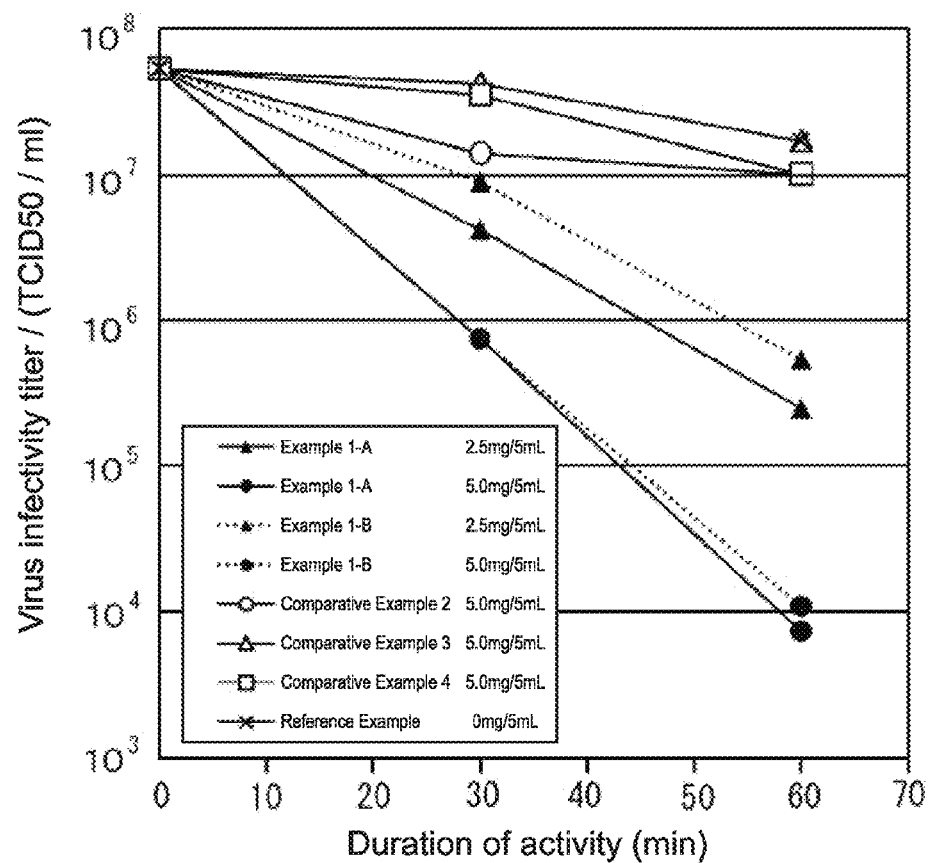
FIG. 5 A graph showing a change in virus infectivity titers to duration of activity of the adsorbents according to Example 1-A, Example 1-B and Comparative Example 1, and masks according to Comparative Examples 2 to 4.

Specifically, a virus infectivity titer of the influenza A was measured based on a TCID50 method. Table 2 and 3 show the results. A unit of the virus infectivity titer is in TCID50/ml. An infectivity titer log reduction value is determined by $log_{10}$ (initial infectivity titer/infectivity titer during duration of activity). An adsorbent concentration is represented by an amount (unit: mg) of the adsorbent added per 5 ml of a buffer solution. In Reference, no adsorbent is added. FIGS. 4 and 5 each show a change in virus infectivity titers to duration of activity.

TABLE 2

| Test sample | Adsorbent concentration | Virus infectivity titer | | | Infectivity titer log reduction value | |
|---|---|---|---|---|---|---|
| | | 0 min (initial) | after 30 min | after 60 min | after 30 min | after 60 min |
| Example 1-A | 2.5 mg/5 ml | $1 \times 10^8$ | $5.6 \times 10^7$ | $9.7 \times 10^6$ | 0.3 | 1.0 |
| | 5.0 mg/5 ml | | $4.5 \times 10^7$ | $6.3 \times 10^5$ | 0.3 | 2.2 |
| Comparative Example 1 | 2.5 mg/5 ml | | $1.4 \times 10^8$ | $1.0 \times 10^8$ | −0.1 | 0.0 |
| | 5.0 mg/5 ml | | $6.3 \times 10^7$ | $4.5 \times 10^7$ | 0.2 | 0.3 |
| Reference Example | — | | — | $2.0 \times 10^8$ | — | −0.3 |

TABLE 3

| Test sample | Adsorbent concentration | Virus infectivity titer | | | Infectivity titer log reduction value | |
|---|---|---|---|---|---|---|
| | | 0 min (initial) | after 30 min | after 60 min | after 30 min | after 60 min |
| Example 1-A | 2.5 mg/5 ml | $5.3 \times 10^7$ | $4.2 \times 10^6$ | $2.5 \times 10^5$ | 1.1 | 2.3 |
| | 5.0 mg/5 ml | | $7.6 \times 10^5$ | $7.4 \times 10^3$ | 1.8 | 3.9 |
| Example 1-B | 2.5 mg/5 ml | | $8.9 \times 10^6$ | $5.4 \times 10^5$ | 0.8 | 2.0 |
| | 5.0 mg/5 ml | | $7.4 \times 10^5$ | $1.1 \times 10^4$ | 1.9 | 3.7 |
| Comparative Example 2 | 5.0 mg/5 ml | | $1.4 \times 10^7$ | $1.0 \times 10^7$ | 0.6 | 0.7 |
| Comparative Example 3 | 5.0 mg/5 ml | | $4.2 \times 10^7$ | $1.7 \times 10^7$ | 0.1 | 0.5 |
| Comparative Example 4 | 5.0 mg/5 ml | | $3.5 \times 10^7$ | $1.0 \times 10^7$ | 0.2 | 0.7 |
| Reference Example | — | | — | $1.7 \times 10^7$ | — | 0.5 |

The adsorbent of Example 1-A showed the infectivity titer log reduction value of "2.2" and "3.9" during duration of activity for 60 min when 5 mg of the adsorbent was added to the 5 ml of the buffer solution. The adsorbent of Example 1-B showed the infectivity titer log reduction value of "3.7" during duration of activity for 60 min when 5 mg of the adsorbent was added to the 5 ml of the buffer solution. In addition, it has been found that the antivirus property is dependent on the adsorbent concentration. It is confirmed that Example 1-A and Example 1-B each has a higher antivirus property than Comparative Example 1, which may be attributed to a difference between the pore diameter distribution in a mesopore area and that in a macropore area. In other words, the adsorbents of Example 1-A and Example 1-B where the Mesopore Area and macropore area are grown adsorb effectively a single virus having a size of about 80 nm to 120 nm and/or a spike protein found on a surface of the virus. As a result, it is estimated that a high antivirus effect could be provided. On the other hand, since the adsorbent of Comparative Example 1 has extremely small mesopore area and macropore area, mainly has the micropore area, and cannot adsorb effectively a single virus having a size of about 80 nm to 120 nm and/or a spike protein found on a surface of the virus. It is estimated that only a low antivirus effect could be provided.

Neuraminidase that is the spike protein present on the surface of the influenza viruses was dissolved into a phosphate buffer so that the concentration of neuraminidase was 20 mg/ml. To 5 ml of a neuraminidase solution, 3 mg of the adsorbents of Example 1-A and Comparative Example 1 were added, respectively. After one hour and three hours, a rate of neuraminidase removal was measured. Table 4 shows the results. The adsorbent of Example 1-A Had A Significantly Higher Rate of neuraminidase removal than that of Comparative Example 1.

TABLE 4

| | Rate of neuraminidase removal (%) | |
|---|---|---|
| | 1 hour | 3 hours |
| Example 1-A | 48.9 | 51.8 |
| Comparative Example 1 | 4.28 | 5.03 |

Figure 6:
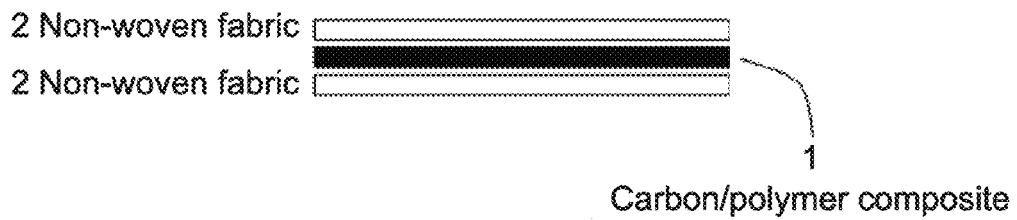
FIG. 6 A diagram showing a schematic section structure of the adsorbent sheet according to Example 1.

FIG. 6 shows a schematic section structure of the adsorbent sheet according to Example 1. The adsorbent sheet according to Example 1 includes the porous carbon material of Example 1 and the support members. Specifically, the adsorbent of Example 1 has a structure that a porous carbon material in a sheet form, i.e., a carbon/polymer composite 1, is sandwiched between a cellulosic support member (non-woven fabric 2) and a support member (non-woven fabric 2). The carbon/polymer composite 1 includes the porous carbon material of Example 1 and the binder. The binder is, for example, carboxyl nitrocellulose. Further, the adsorbent sheet can have the embodiments that the porous carbon material of Example 1 can be applied to the support members, or the porous carbon material of Example 1 may be kneaded with the support member.

EXAMPLE 2

Figure 7:
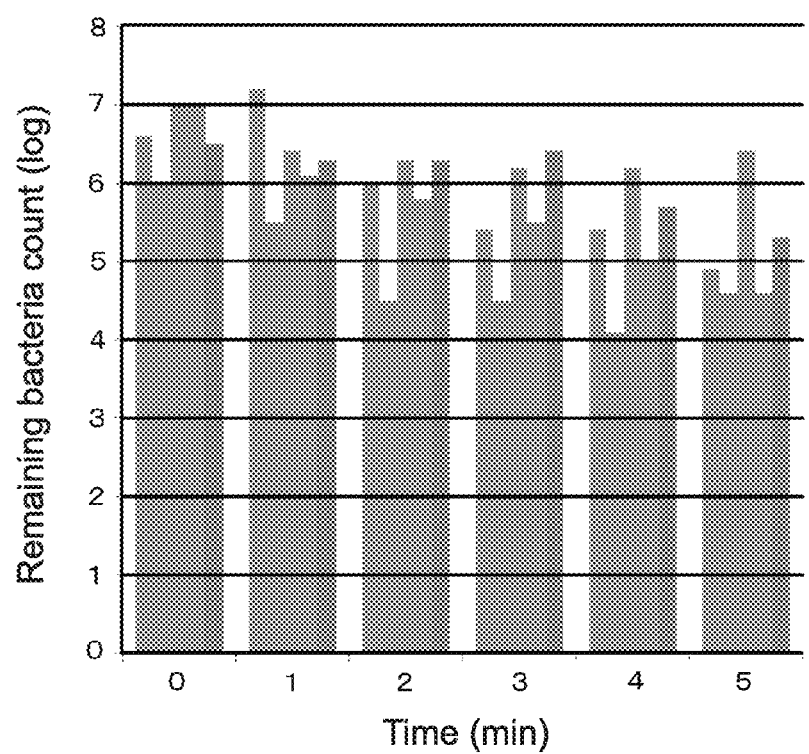
FIG. 7 A graph showing various remaining bacteria counts per minute (logarithmic expression) by comparison.

In Example 2, the bacterial adsorption capability against various bacteria was evaluated. In Example 2, the adsorbent of Example 1-A was used. To 5 ml of each test bacterial liquid, 5 mg of the adsorbent of Example 2 was added to provide a test liquid. Then, the test liquid was shaken (120 rpm) at 25° C. for a predetermined time, and was immediately thereafter centrifuged (2000 rpm, 10 seconds) to precipitate the adsorbent. Then, 1 ml of a supernatant was taken, and was added to 9 ml of a SCDLP bouillon culture media (Eiken Chemical Co., Ltd.). Thus-obtained sample liquid was measured and determined for bacteria numbers per ml of the supernatant. A minimum determination limit is 100 CFU/ml. A similar operation was repeated to provide a control except that no adsorbent is added. Table 5 shows the obtained test results. FIG. 7 shows various remaining bacteria counts in the adsorbent of Example 2 per minute (logarithmic expression) by comparison. In FIG. 7, five bar charts are shown in each time. There are the test results about *Staphylococcus aureus*, Enterohemorrhagic *E. coli*, lactic acid bacteria, *Citrobacter*, and enterococci from left to right. As the control, the value at 0 min was $4.0 \times 10^7$, and the value at 5 min was $2.8 \times 10^6$.

TABLE 5

|  | Time | | | | | |
| --- | --- | --- | --- | --- | --- | --- |
|  | 0 min | 1 min | 2 min | 3 min | 4 min | 5 min |
| *Staphylococcus aureus* | $4.8 \times 10^6$ | $1.6 \times 10^7$ | $1.1 \times 10^6$ | $2.9 \times 10^5$ | $2.8 \times 10^5$ | $9.0 \times 10^4$ |
| Enterohemorrhagic *E. coli* | $1.1 \times 10^6$ | $3.3 \times 10^5$ | $3.2 \times 10^4$ | $3.8 \times 10^4$ | $1.3 \times 10^4$ | $4.4 \times 10^4$ |
| Lactic acid bacteria | $1.1 \times 10^7$ | $2.7 \times 10^6$ | $2.2 \times 10^6$ | $1.6 \times 10^6$ | $1.6 \times 10^6$ | $3.1 \times 10^6$ |
| *Citrobacter* | $1.2 \times 10^7$ | $1.5 \times 10^6$ | $7.0 \times 10^5$ | $3.4 \times 10^5$ | $1.1 \times 10^5$ | $4.8 \times 10^4$ |
| Enterococci | $3.6 \times 10^6$ | $2.4 \times 10^6$ | $2.1 \times 10^6$ | $2.9 \times 10^6$ | $5.6 \times 10^5$ | $2.3 \times 10^5$ |

The test results reveal that the adsorbent of Example 2 adsorbs the bacteria and decreases the remaining bacteria counts. In addition, the remaining bacteria counts are decreased in a short time such as 1 to 5 minutes. Thus, when bacteria containing water is treated with the adsorbent of Example 2, the bacteria counts can be effectively decreased in a short time to improve water quality. In particular, the adsorbent well adsorbs *Staphylococcus aureus* that can be a causative bacterium, Enterohemorrhagic *E. coli* that produces toxins, *Citrobacter* that is contamination bacterium, and less adsorbs lactic acid bacteria that are intestinal good bacteria and enterococci that are normal inhabitants. It was confirmed that the adsorbent had selectivity.

EXAMPLE 3

In Example 3, the adsorbent of Example 1-A was used to perform an adsorption test against *E. coli*. Specifically, to 1 ml of sterile distilled water, 100 g of the adsorbent of Example 3 was added, and 0.1 ml of a test bacterial liquid was further added. A thus-obtained test liquid was shaken (100 rpm) at 25° C. 1 ml of the test liquid was filtered with a membrane filter, and was then washed with 2 ml of sterile distilled water. Then, the SCDLP bouillon culture media was added thereto as in Example 2 to a total volume of 10 ml to provide a sample liquid. *E. coli* numbers were determined per ml of the sample liquid. A minimum determination limit is 100 CFU/ml. The adsorbent of Comparative Example 1 was similarly tested. Table 6 shows the results. It reveals that the adsorbent of Example 3 effectively adsorbs *E. coli*.

TABLE 6

|  | Time | |
| --- | --- | --- |
|  | 0 min | 5 min |
| Example 3 | $4.8 \times 10^4$ | $1.0 \times 10$ |
| Comparative Example 1 | $4.8 \times 10^4$ | $1.5 \times 10^3$ |
| Control | $4.8 \times 10^4$ | $7.4 \times 10^4$ |

EXAMPLE 4

In Example 4, the adsorbent of Example 1-A was used to evaluate the adsorption capability against feline caliciviruses (size: about 30 nm to 40 nm) as alternatives for noroviruses (size: about 30 nm). The norovirus is a virus having about 7500 bases and no envelops that is categorized as a plus single-strand RNA virus. Specifically, a virus infectivity titer was measured based on a TCID50 method as in Example 1. Table 7 shows the obtained test results. A unit of the virus infectivity titer is in TCID50/ml. An infectivity titer log reduction value is determined by $\log_{10}$ (initial infectivity titer/infectivity titer during duration of activity). An adsorbent concentration is represented by an amount (unit: mg) of the adsorbent added per 5 ml of a buffer solution. The adsorbent of Comparative Example 1 was similarly tested.

TABLE 7

| Test sample | Adsorbent concentration | Virus infectivity titer | | | Infectivity titer log reduction value | |
| --- | --- | --- | --- | --- | --- | --- |
|  |  | 0 min (initial) | after 30 min | after 60 min | after 30 min | after 60 min |
| Example 4 | 5.0 mg/ml | $1.1 \times 10^6$ | $1.2 \times 10^3$ | $7.6 \times 10^2$ | 3.0 | 3.2 |
| Comparative Example 1 | 5.0 mg/ml |  | $8.4 \times 10^3$ | $2.0 \times 10^3$ | 2.1 | 2.7 |
| Control | — |  | — | $1.0 \times 10^5$ | — | 1.0 |

Since the viruses are small, the infectivity titer log reduction value after 60 min in Example 4 is close to that in Comparative Example 1. However, the infectivity titer log reduction value after 30 min in Example 4 is about 1 smaller than that in Comparative Example 1. It reveals that Example 4 shows higher adsorption capability than Comparative Example 1. Also, it reveals that Example 4 shows excellent adsorption capability not only for the influenza viruses, but also for smaller viruses.

The present disclosure has been described based on the embodiment thereof, and the present disclosure is not limited to the embodiments and may be modified in various ways. While the chaff is used as the raw material of the porous carbon material in Examples, other plants may be used. For example, other usable plants include straws, reeds, stems of Wakame seaweed, terrestrial vascular plants, ferns, bryophytes, algae, and marine algae. Those plants may be used alone, and plural types of such plants may alternatively be used in combination. Specifically, chaff of paddy (e.g., Isehikari produced in Kagoshima prefecture in Japan) may be the plant-based material which is the raw material of the porous carbon material. The chaff may be carbonized into a carbonaceous substance (a porous carbon material precursor), and the carbonaceous substance may be treated with an acid to obtain the porous carbon material. Alternatively, gramineous reeds may be the plant-based material is the raw material of the porous carbon material. The gramineous reeds may be carbonized into a carbonaceous substance (a porous carbon material precursor), and the carbonaceous substance may be treated with an acid to obtain the porous carbon material. Advantages similar to those described above were achieved by the porous carbon material obtained by treating a material using alkali (base) such as a water solution of sodium hydroxide instead of a water solution of hydrofluoric acid.

Alternatively, stems of Wakame seaweed (cropped in Sanriku, Iwate prefecture in Japan) may be the plant-based material which is the raw material of the porous carbon material. The stems of Wakame seaweed may be carbonized into a carbonaceous substance (porous carbon material precursor), and the carbonaceous substance may be treated with an acid to obtain the porous carbon material. Specifically, the stems of Wakame seaweed are heated at a temperature of, for example, 500° C. and carbonized. The stems of Wakame seaweed may be treated with alcohol before the heating. Specifically, the raw material may be immersed in ethyl alcohol or the like. As a result, moisture included in the raw material is reduced, and the process also allows elution of elements other than carbon and mineral components which will otherwise be included in the porous carbon material finally obtained. The treatment with alcohol suppresses the generation of gasses during the carbonizing process. More specifically, stems of Wakame seaweed are immersed in ethyl alcohol for 48 hours. It is desirable to perform an ultrasonic process on the material in ethyl alcohol. The stems of Wakame seaweed are then carbonized by being heated at 500° C. for 5 hours in a flow of nitrogen gas to obtain a carbide. Such a process (preliminary carbonizing process) can reduce or eliminate tar components that would be produced at the subsequent carbonizing step. Thereafter, 10 grams of the carbide is put in a crucible made of alumina, and the temperature of the carbide is raised to 1000° C. at a rate of 5° C./min. in a flow of nitrogen gas (10 liters/min). The carbide is carbonized at 1000° C. for 5 hours and converted into a carbonaceous substance (porous carbon material precursor), and the substance is cooled down to room temperature. The nitrogen gas is kept flowing during the carbonization and cooling. Next, the porous carbon material precursor is acid-treated by immersion in a water solution of hydrofluoric acid of 46 vol % overnight, and the precursor is washed with water and ethyl alcohol until it reaches a pH of 7. Finally, the precursor is dried so that a porous carbon material will be obtained.

DESCRIPTION OF REFERENCE NUMERALS 1 carbon/polymer composite
2 non-woven fabric

The invention claimed is:

1. A method, comprising:
providing a porous carbonaceous material comprising pores having diameters in a range from $1\times10^{-9}$ m to $5\times10^{-7}$ m, wherein the porous carbonaceous material has a specific surface area of 10 m$^2$/g or more as measured by a nitrogen BET method, a total pore volume of 0.1 cm$^3$/g or more as determined by Non Localized Density Functional Theory, and one or more peaks between 70 nm and 180 nm in a pore diameter distribution as determined by Non Localized Density Functional Theory; and
adsorbing a virus and/or a bacterium to the porous carbonaceous material.

2. The method according to claim 1, wherein the porous carbonaceous material has at least one peak in a pore diameter distribution in a range from 3 nm to 20 nm as determined by Non Localized Density Functional Theory, and a ratio of the volume of pores with diameters in the range from 3 nm to 20 nm to the total pore volume of 0.2 or more.

3. The method according to claim 2, wherein the porous carbonaceous material comprises mesopores having a pore diameter in a range of about 2 nm to about 50 nm and macropores having a pore diameter greater than about 50 nm.

4. The method according to claim 3, wherein the porous carbonaceous material further comprises micropores having a pore diameter less than about 2 nm.

5. The method according to claim 1, wherein the porous carbonaceous material has a pore volume of 0.5 cm$^3$/g or more as measured by a BJH method.

6. The method according to claim 1, wherein the porous carbonaceous material has a pore volume of 4.12 cm$^3$/g or more as measured by a mercury intrusion method.

7. The method according to claim 1, wherein the porous carbonaceous material has a pore volume of 0.515 cm$^3$/g or more as measured by an MP method.

8. The method according to claim 1, wherein:
the porous carbonaceous material is made from a plant-based material; and
the plant-based material comprises chaff, straws, coffee beans, tea leaves, sugar canes, corns, fruit peels, reeds, and/or Wakame seaweed stems.

9. A method, comprising:
providing a carbon/polymer composite, wherein the carbon/polymer composite comprises:
a porous carbonaceous material comprising pores having diameters in a range from $1\times10^{-9}$ m to $5\times10^{-7}$ m, wherein the porous carbonaceous material has a specific surface area of 10 m$^2$/g or more as measured by a nitrogen BET method, a total pore volume of 0.1 cm$^3$/g or more as determined by Non Localized Density Functional Theory, at least one peak in a pore diameter distribution in a range from 3 nm to 20 nm as determined by Non Localized Density Functional Theory, a ratio of the volume of pores with diameters in the range from 3 nm to 20 nm to the total pore volume of 0.2 or more, and one or more peaks between 70 nm and 180 nm in a pore diameter distribution as determined by Non Localized Density Functional Theory; and
a binder; and
adsorbing a virus and/or a bacterium to the carbon/polymer composite.

10. The method according to claim 9, wherein the porous carbonaceous material comprises mesopores having a pore diameter in a range of about 2 nm to about 50 nm and macropores having a pore diameter greater than about 50 nm.

11. The method according to claim 10, wherein the porous carbonaceous material further comprises micropores having a pore diameter less than about 2 nm.

12. The method according to claim 9, wherein the porous carbonaceous material has a pore volume of 0.5 cm$^3$/g or more as measured by a BJH method.

13. The method according to claim 9, wherein the porous carbonaceous material has a pore volume of 4.12 cm³/g or more as measured by a mercury intrusion method.

14. The method according to claim 9, wherein the porous carbonaceous material has a pore volume of 0.515 cm³/g or more as measured by an MP method.

15. The method according to claim 9, wherein:
the porous carbonaceous material is made from a plant-based material; and
the plant-based material comprises chaff, straws, coffee beans, tea leaves, sugar canes, corns, fruit peels, reeds, and/or Wakame seaweed stems.

16. A method, comprising:
providing an adsorbent sheet, wherein the adsorbent sheet comprises:
a porous carbonaceous material comprising pores having diameters in a range from $1\times10^{-9}$ m to $5\times10^{-7}$ m, wherein the porous carbonaceous material has a specific surface area of 10 m²/g or more as measured by a nitrogen BET method, a total pore volume of 0.1 cm³/g or more as determined by Non Localized Density Functional Theory, at least one peak in a pore diameter distribution in a range from 3 nm to 20 nm as determined by Non Localized Density Functional Theory, a ratio of the volume of pores with diameters in the range from 3 nm to 20 nm to the total pore volume of 0.2 or more, and one or more peaks between 70 nm and 180 nm in a pore diameter distribution as determined by Non Localized Density Functional Theory; and
a support member; and
adsorbing a virus and/or a bacterium to the adsorbent sheet.

17. The method according to claim 16, wherein the porous carbonaceous material comprises mesopores having a pore diameter in a range of about 2 nm to about 50 nm and macropores having a pore diameter greater than about 50 nm.

18. The method according to claim 17, wherein the porous carbonaceous material further comprises micropores having a pore diameter less than about 2 nm.

19. The method according to claim 16, wherein:
the porous carbonaceous material is made from a plant-based material; and
the plant-based material comprises chaff, straws, coffee beans, tea leaves, sugar canes, corns, fruit peels, reeds, and/or Wakame seaweed stems.

20. The method according to claim 16, wherein the support member is composed of a non-woven fabric.

* * * * *